United States Patent [19]

Garst

[11] Patent Number: 5,451,686

[45] Date of Patent: Sep. 19, 1995

[54] 3 AND 5 ALKYL AND PHENYL 4-(HYDROXY OR ACYLOXY)-ALKYL SUBSTITUTED 2(5H)-FURANONES AS ANTI-INFLAMMATORY AGENTS

[75] Inventor: Michael E. Garst, Newport Beach, Calif.

[73] Assignee: Allergan, Inc., Irvine, Calif.

[21] Appl. No.: 228,241

[22] Filed: Apr. 15, 1994

[51] Int. Cl.$^6$ ............... C07F 9/09; C07D 307/40
[52] U.S. Cl. ................... 549/222; 549/321; 549/323
[58] Field of Search ............ 549/323, 321, 222

[56] References Cited

U.S. PATENT DOCUMENTS

| | | | |
|---|---|---|---|
| 2,359,096 | 9/1944 | Elderfield | 260/239.5 |
| 2,359,208 | 9/1944 | Elderfield | 260/344 |
| 4,447,445 | 5/1984 | Jacobs | 424/279 |
| 4,786,651 | 11/1988 | Wheeler | 514/460 |
| 4,789,749 | 12/1988 | Jacobs et al. | 549/313 |
| 4,855,320 | 8/1989 | Chatterjee et al. | 514/473 |
| 4,874,782 | 10/1989 | Bonjouklian et al. | 514/473 |
| 4,916,241 | 4/1990 | Hayward et al. | 549/313 |
| 4,935,530 | 6/1990 | Lee | 549/214 |
| 5,013,850 | 5/1991 | Lee | 549/222 |
| 5,037,811 | 8/1991 | Lee | 514/99 |
| 5,043,457 | 8/1991 | Lee | 549/222 |
| 5,045,564 | 9/1991 | Lee | 514/471 |
| 5,082,954 | 1/1992 | Lee | 549/214 |
| 5,112,853 | 5/1992 | Garst | 514/443 |
| 5,134,128 | 7/1992 | Lee et al. | 514/63 |
| 5,169,963 | 12/1992 | Lee | 549/222 |
| 5,171,863 | 12/1992 | Lee et al. | 549/214 |
| 5,171,864 | 12/1992 | Lee | 549/222 |
| 5,183,906 | 2/1993 | Lee et al. | 549/218 |
| 5,212,172 | 5/1993 | Lee | 514/231.5 |
| 5,225,571 | 7/1993 | Lee | 549/222 |
| 5,258,400 | 11/1993 | Garst et al. | 514/443 |
| 5,268,387 | 12/1993 | Garst | 514/461 |
| 5,298,633 | 3/1994 | Lee et al. | 549/484 |
| 5,322,953 | 6/1994 | Lee et al. | 549/214 |

FOREIGN PATENT DOCUMENTS

| | | | |
|---|---|---|---|
| 133376 | 2/1985 | European Pat. Off. | C07D 307/58 |
| 209274 | 1/1987 | European Pat. Off. | C07D 307/60 |
| 295056 | 6/1987 | European Pat. Off. | C07D 307/60 |
| 369811 | 5/1990 | European Pat. Off. | C07D 307/60 |

*Primary Examiner*—C. Warren Ivy
*Assistant Examiner*—A. A. Owens
*Attorney, Agent, or Firm*—Gabor L. Szekeres; Robert J. Baran; Martin A. Voet

[57] ABSTRACT

Novel anti-inflammatory furanone compounds have the following formula:

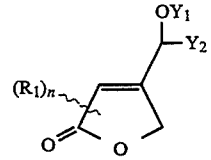

where $R_1$ independently is H, or alkyl of 1 to 9 carbons and n is an integer having the values of 1 or 2, and where when n is 1 the $R_1$ group is attached to the 5 position of the 2-furanone, when n is 2 then $R_1$ is attached to both the 3 and 5 positions, with the proviso that when n is 1 then $R_1$ is not H; $Y_1$ is H, alkyl of 1 to 20 carbons, phenyl $C_1$–$C_{20}$ alkyl, $C_1$–$C_{20}$ alkenyl containing one or more olefinic bonds, where $R_3$ is H, $C_1$–$C_{20}$ alkyl, $C_1$–$C_{20}$ alkenyl containing one or more olefinic bonds, phenyl, halogen substituted phenyl or $C_1$–$C_6$ alkyl substituted phenyl, with the proviso that when $Y_1$ is CO—OR$_3$ or CONHR$_3$ then $R_3$ is not hydrogen; $Y_2$ is H, an alkyl group of 1 to 25 carbons, or phenyl.

22 Claims, No Drawings

3 AND 5 ALKYL AND PHENYL 4-(HYDROXY OR ACYLOXY)-ALKYL SUBSTITUTED 2(5H)-FURANONES AS ANTI-INFLAMMATORY AGENTS

BACKGROUND OF THE INVENTION

1. Field of the Invention

The present invention is directed to novel 2- and 5-alkyl and phenyl substituted 4-(1-hydroxy-, 1-acyloxy-, or 1-carbamoyloxy)-2(5H)-furanones which compounds are active as anti-inflammatory agents. The present invention is also directed to pharmaceutical compositions which comprise one or more of the novel compounds of the invention, to the methods of using these pharmaceutical compositions, and to the chemical processes of making the novel compounds.

2. Brief Description of the Prior Art

Manoalide is a compound isolated from a marine sponge [E. D. de Silva et al., *Tetrahedron Letters* 21:1611–1614 (1980)] which has anti-inflammatory, immunosuppressive and analgesic properties. Manoalide the structure of which is shown below, includes a 5-hydroxy-2(5H)-furanone moiety, attached in the 4-position of the furanone ring to the rest of the molecule. Certain analogs of manoalide, such as seco-manoalide and dehydro-seco-manoalide also have anti-inflammatory activity. For further description of the biological activity of manoalide and some of its derivatives reference is made to U.S. Pat. Nos. 4,447,445, 4,786,651, 4,789,749 and to European Patent Application No. 0 133 376 (published on Feb. 20, 1985).

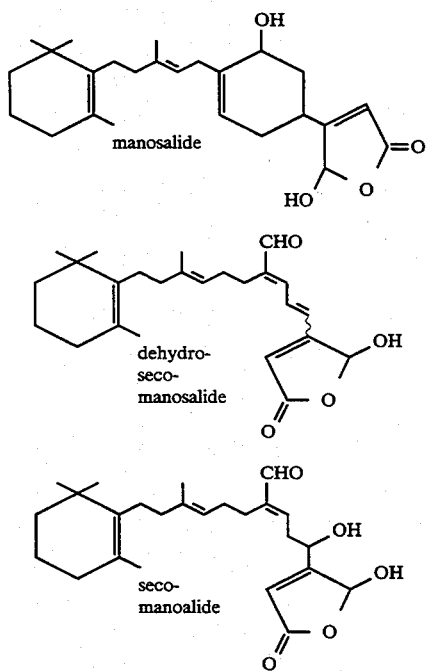

Synthetic analogs of manoalide, particularly analogs having various substituents on the furanone moiety of manoalide, are described in several United States patents and applications for United States patent assigned to the same assignee as the present application. Among these, U.S. Pat. No. 5,045,564 discloses 4-substituted 2-5(H)-furanones as anti-inflammatory and calcium channel antagonist agents. U.S. Pat. No. 5,183,906 (issued on Feb. 2, 1993) 3 and 5 alkyl and phenyl 4-(1-hydroxy, 1-acyloxy or 1-carbamoyloxy)-5-hydroxy-2-furanones, as anti-inflammatory and calcium channel antagonist agents.

U.S. Pat. No. 5,268,387 describes a method for treating an imbalance between bone production and resorption with furanone compounds, the general examples of which include 3 and 5 alkyl and phenyl 4-(1-hydroxy, 1-acyloxy or 1-carbamoyloxy)-2-furanones, and the specific examples of which include 3 and 5 alkyl and phenyl 4-(1-hydroxy, 1-acyloxy or 1-carbamoyloxy)-5-hydroxy-2-furanones.

European Patent Application No. 0 534 907 A1 (published Mar. 31, 1993) discloses 3,5-dialkyl, 3,5,-dialkyl-4-hydroxy, and 3,4,5-trialkyl-2-furanones as agents for treatment of autoimmune diseases.

As further general background Published European Patent Application No. 0 295 056 is noted, which discloses 4-substituted 5-hydroxy-2(5H)-furanones having anti-inflammatory, immunosuppressive and anti-proliferative activity where the substituents in the 4 position are a variety 1-hydroxyalkyl, 1-acyloxy-alkyl and 1-carbamoyloxy-alkyl groups.

U.S. Pat. No. 4,855,320 discloses 5-arylalkyl-4-alkoxy-2(5H)-furanones as anti-convulsive and anti-epileptic agents.

Published European Patent Application No. 0 209 274 discloses 4-alkyl-5-hydroxy-2(5H)-furanones as anti-inflammatory and anti-allergy agents.

Chemical Abstracts Volume 107 236559t (1987) discloses 4-acyloxy 5-hydroxy-2(5H)-furanones.

2-Substituted 4-furaldehydes (5-substituted 3-furaldehydes) are described in U.S. Pat. No. 4,935,530.

SUMMARY OF THE INVENTION

The present invention covers compounds of Formula

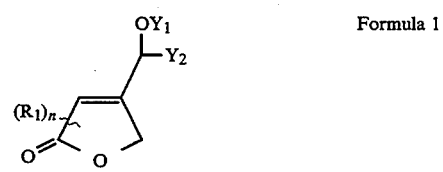

Formula 1 where $R_1$ independently is H, phenyl, $C_1$–$C_6$ alkyl substituted phenyl, halogen substituted phenyl, or alkyl of 1 to 9 carbons and n is an integer having the values of 1 or 2, and where when n is 1 the $R_1$ group is attached either to the 3 or to the 5 position of the 2-furanone, when n is 2 then $R_1$ is attached to both the 3 and 5 positions, with the proviso that the substituents in the 3 and 5 positions both cannot be hydrogen;

$Y_1$ is H, alkyl of 1 to 20 carbons, phenyl $C_1$–$C_{20}$ alkyl, $C_1$–$C_{20}$ alkenyl containing one or more olefinic bonds, $PO(OH)_2$, $PO(OH)OR_2$, $PO(OH)R_2$, $PO(OR_2)_2$, where $R_2$ is independently alkyl of 1 to 20 carbons, phenyl, halogen substituted phenyl or $C_1$–$C_6$ alkyl substituted phenyl, further $Y_1$ is CO—$R_3$, CO—$OR_3$, CONHR$_3$, SO$_2$R$_3$, SO$_2$NHR$_3$, (CH$_2$)$_p$—O—R$_3$, or (CH$_2$)$_p$—O—(CH$_2$)$_m$—O—R$_3$, where p, and m, are integers and are independently 1 to 20 and R$_3$ is H, $C_1$–$C_{20}$ alkyl, $C_1$–$C_{20}$ alkenyl containing one or more olefinic bonds, phenyl, halogen substituted phenyl or $C_1$–$C_6$ alkyl substituted phenyl, with the proviso that when $Y_1$ is $CO-OR_3$ or $CONHR_3$ then $R_3$ is not hydrogen;

$Y_2$ is H, an alkyl group of 1 to 25 carbons, phenyl, naphthyl, phenyl ($C_1$-$C_{20}$)alkyl-, naphthyl ($C_1$-$C_{20}$)alkyl-, halogen substituted phenyl, $C_1$-$C_6$ alkyl substituted phenyl, halogen substituted naphthyl, $C_1$-$C_6$ substituted naphthyl.

The present invention also covers salts of the above-defined compounds, formed with pharmaceutically acceptable acids or bases, as applicable.

In a second aspect the present invention relates to pharmaceutical formulations comprising one or more compounds of Formula 1 (or pharmaceutically acceptable salts thereof) in admixture with a pharmaceutically acceptable excipient, for the purpose of treating certain conditions, syndromes or diseases in mammals, including humans. The compounds of the invention have anti-inflammatory, immunosuppressant and anti-proliferative activity without having significant contact sensitizing activity on the mammalian skin. Therefore, the compounds are useful for treating in mammals (including humans) inflammation, rheumatoid arthritis, osteoarthritis, rheumatic carditis, ocular and dermal inflammatory diseases, autoimmune diseases such as allergic diseases, bronchial asthma and myasthenia gravis, and for suppressing unwanted immune responses and retarding proliferation of cell.

In still another aspect, the present invention relates to the processes of making the compounds of Formula 1. In general terms, these processes, shown in a summarized fashion in Reaction Scheme 1 comprise the step of reducing a compound of Formula 2 to provide a compound of Formula 1. As the reaction scheme shows, this reduction results in the replacement of the 5-hydroxy function of the 2-furanone moiety with a hydrogen group, thereby providing a "5-deshydroxy" compound. Generally speaking, the compounds of Formula 2 are obtained in accordance with the teachings and synthetic procedures described in U.S. Pat. No. 5,183,906 the specification of which is hereby expressly incorporated by reference. Compounds of Formula 1 where the $Y_1$ group is other than hydrogen can also be obtained by introducing the $Y_1$ substituent into the corresponding hydroxy compound (where $Y_1$ is hydrogen) by alkylation, acylation reaction with an isocyanate, or other reaction known in the art and appropriate to introduce the $Y_1$ group into an alcohol such as the $Y_2CH(OH)$- moiety of the substituted furanones of this invention.

Reaction Scheme 1

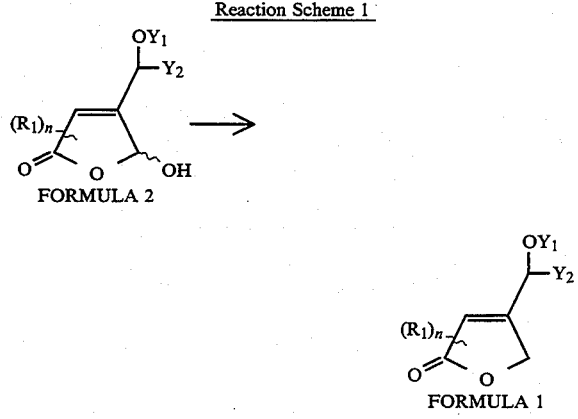

FORMULA 2

FORMULA 1

General Embodiments

Definitions

The terms "ester", "amine", "amide", "ether" and all other terms and terminology used here, (unless specifically defined in the present description) refer to and cover any compounds falling within the respective term as that term is classically used in organic chemistry.

Unless specifically noted otherwise, preferred esters are derived from the saturated aliphatic alcohols or acids of ten or fewer carbon atoms or from the cyclic or saturated aliphatic cyclic alcohols and acids of 5 to 10 carbon atoms. Particularly preferred aliphatic esters are those derived from lower alkyl acids or alcohols. Also preferred are the phenyl or lower alkylphenyl esters.

The term "alkyl" as used in the present description and claims includes straight chain alkyl groups, branched chain alkyl groups, cycloalkyl groups, alkyl substituted cycloalkyl groups, and cycloalkyl substituted alkyl groups. Unless the number of carbons is otherwise specified, "lower alkyl" means the former broad definition of "alkyl" groups but with the restriction that the group has 1 to 6 carbon atoms.

Unless specifically noted otherwise, the term "long chain alkyl" also means the former broad definition of "alkyl" groups but with the restriction that the group has no less than 4 carbon atoms, and no more than approximately 25 carbon atoms.

Unless specifically noted otherwise, preferred amides are the mono- and di-substituted amides derived from the saturated aliphatic radicals of ten or fewer carbon atoms, or the cyclic or saturated aliphaticcyclic radicals of 5 to 10 carbon atoms.

Certain compounds of the invention contain a chiral center at the alpha carbon in the side chain on the 4-position of the 2(5H)-furanone moiety. Other compounds of the invention may contain more than one chiral center. Accordingly, the compounds of the invention may be prepared as mixtures of enantiomeric compounds (where the enantiomers may or may not be present in equal amounts) or as optically pure enantiomers. When there is more than one chiral center, the compounds of the invention may also be prepared as mixtures of diastereomers, or as pure diastereomers, and each diastereomer itself may be a mixture of enantiomers in 1:1, or other, ratios. Alternatively, each diastereomeric compound may be sterically and optically pure. However, all of the above-noted forms, including optically pure enantiomers and mixtures thereof, as well as all diastereomers, are within scope of the present invention.

Some of the compounds of the invention may have cis and trans stereoisomers. The scope of the invention includes both pure stereoisomers as well as mixtures thereof.

A pharmaceutically acceptable salt may be prepared for any compound of this invention having a functionality capable of forming such salt, for example an acid or an amine functionality. A pharmaceutically acceptable salt may be any salt which retains the activity of the parent compound and does not impart any deleterious or untoward effect on the subject to which it is administered and in the context in which it is administered.

Such a salt may be derived from any organic or inorganic acid or base. The salt may be a mono or polyvalent ion. Of particular interest where the acid function is concerned are the inorganic ions, sodium, potassium, calcium, and magnesium. Organic amine salts may be made with amines, particularly ammonium salts such as mono-, di- and trialkyl amines or ethanol amines. Salts may also be formed with caffeine, tromethamine and similar molecules. Where there is a nitrogen sufficiently basic as to be capable of forming acid addition salts, such may be formed with any inorganic or organic acids or alkylating agent such as methyl iodide. Preferred salts are those formed with inorganic acids such as hydrochloric acid, sulfuric acid or phosphoric acid. Any of a number of simple organic acids such as mono-, di- or tri-acid may also be used.

The preferred compounds of the present invention, with reference to Formula 1 and with respect to the $R_1$ substituent are those where $R_1$ is alkyl, more preferably alkyl of 1 to 6 carbons, and still more more preferably methyl. Also preferred are the compounds where $R_1$ is phenyl.

Regarding the $Y_1$ substituent, compounds are preferred in accordance with the present invention where the $Y_1$ is H, or an acyl group, designated $CO-R_3$ in Formula 1. More preferably, the acyl group is acetoxy, or a long chain lipophilic acyl group where the $R_3$ group is long chain alkyl. Especially preferred are compounds where the acyl group is lauroyl.

Regarding the $Y_2$ substitutent, compounds are preferred in accordance with the present invention where $Y_2$ is long chain alkyl, preferably alkyl having 8 to 16 carbons, even more preferably alkyl having 12 carbons. Compounds are also preferred in accordance with the present invention where $Y_2$ is hydrogen, provided the $Y_1$ group is then a long chain lipophilic acyl group. The most preferred compounds of the invention are listed below with reference to Formula 1:

Compound 1: $n=1$, $R_1=5$-methyl, $Y_1=CH_3CO$; $Y_2=(CH_2)_{11}-CH_3$

Compound 2: $n=1$, $R_1=3$-methyl, $Y_1=CH_3CO$; $Y_2=(CH_2)_{11}-CH_3$

Compound 3: $n=1$, $R_1=5$-methyl, $Y_1=H$; $Y_2=(CH_2)_{11}-CH_3$

Compound 4: $n=2$, $R_1=3$-phenyl, $R_1=5$-methyl $Y_1=CO(CH_2)_{10}CH_3$, $Y_2=H$ The compounds of the present invention are useful in pharmaceutical compositions to produce anti-inflammatory, immunosuppressant and anti-proliferative activity. The diseases, syndromes or conditions of mammals (including humans) which can be treated with pharmaceutical compositions containing one or more compounds of the invention (or salts thereof) include: inflammation, rheumatoid arthritis, osteoarthritis, rheumatic carditis, ocular and dermal inflammatory diseases, autoimmune diseases such as allergic diseases, bronchial asthma and myasthenia gravis, unwanted immune responses and unwanted proliferation of cells, psoriasis, acne, atopic diseases and allergic conjunctivitis.

The compounds of this invention are tested as inhibitors of the enzyme phospholipase $A_2$ in vitro, and for reduction of inflammation in the mouse ear anti-inflammatory assay in vivo.

The compounds of the invention modify calcium homeostasis. This activity is shown by effect on intracellular calcium levels in experiments using gastric glands, spleen cells, epithelial cells, $GH_3$cells, etc. Calcium is inhibited from entering through the plasma membrane calcium channels and calcium release from intracellular stores is also blocked. Modification of calcium homeostasis is expected to have application in diseases of the nervous system involving modification of membrane lipids or transmitter release (Parkinson's, Alzheimer's), diseases of the cardiovascular system involving application of cardiac or vascular smooth muscle contractility and platelet aggregation (hypertension, cardiac infarction and atherosclerosis), diseases of the gastrointestinal tract such as ulcer disease, diarrhea, motility due to secretion of acid or $Cl^-$, diseases of the kidney involving renal handling of fluid and electrolytes (metabolic acidosis, alkalosis), and disease of abnormal growth (neoplasia, psoriasis).

The compounds of this invention have activity which is similar to that of manoalide, that is the compounds appear to be devoid of the endocrine properties of the glucocorticoids while having anti-inflammatory and immunosuppressive properties. In addition those compounds of the invention which have a substituent in the 5 position lack certain disadvantageous skin-sensitizing properties of certain 5-hydroxy-2(5H)-furanone derivatives which otherwise have anti-inflammatory activity. Still further, as the data below indicate the compounds of the invention are essentially inactive in the phospholipase $A_2$ assay, but active in the $Ca^{++}$ channel inhibition assay. Thus, the compounds are selective inhibitors of the $Ca^{++}$ channel. While, generally speaking activity, in either the phospholipase $A_2$ or in the $Ca^{++}$ channel assay are hallmarks of anti-inflammatory activity, selectivity for $Ca^{++}$ channel inhibition is also a highly desirable pharmacological property. The $Ca^{++}$ channel selectivity of the compounds of the present invention is unusual and certainly surprising in light of the known prior art.

In the methods of this invention, the compounds of the invention are administered to mammals, including humans, in an effective amount to produce the desired activity, preferably in an amount of about 0.05 to 100 mg per day per kilogram of body weight. The amount of the compound depends upon the disease or condition being treated, the severity thereof, the route of administration and the nature of the host. The compounds may be administered topically, orally, parenterally or by other standard routes of administration.

Pharmaceutical compositions of this invention comprise compounds of Formula 1, and pharmaceutical carriers suitable for the route of administration. Standard methods for formulating pharmaceutical compositions of this type may be found in *Remington's Pharmaceutical Sciences*, Mack Publishing Company, Easton, Pa.

For topical administration, the pharmaceutical composition may be in the form of a salve, cream, ointment, spray, powder or the like. Standard pharmaceutical carriers for such compositions may be used. Preferably, compositions for topical administration will contain 0.05–5% of the active ingredient.

A typical cream formulation may contain the following:

| Ingredient | Parts by Weight |
| --- | --- |
| Water/glycol mixture (15% or more glycol) | 50–99 |
| Fatty alcohol | 1–20 |
| Non-ionic surfactant | 0–10 |
| Mineral oil | 0–10 |
| Typical pharmaceutical adjuvants | 0–5 |
| Active ingredient | 0.05–5 |

A typical ointment formulation may contain the following:

| Ingredients | Parts by Weight |
| --- | --- |
| White petrolatum | 40–94 |
| Mineral oil | 5–20 |
| Glycol solvent | 1–15 |
| Surfactant | 0–10 |
| Stabilizer | 0–10 |
| Active ingredient | 0.05–5 |

For oral administration, suitable pharmaceutical carriers include mannitol, lactose, starch, magnesium stearate, talcum, glucose and magnesium carbonate. Oral compositions may be in the form of tablets, capsules, powders, solutions, suspensions, sustained release formulations, and the like.

A typical tablet or capsule may contain the following:

| Ingredients | Percent w/w |
| --- | --- |
| Lactose, spray-dried | 40–99 |
| Magnesium stearate | 1–2 |
| Cornstarch | 10–20 |
| Active ingredient | 0.001–20 |

Parenteral compositions are prepared in conventional suspension or solution forms, as emulsions or as solid forms for reconstruction. Suitable carriers are water, saline, dextrose, Hank's solution, Ringer's solution, glycerol, and the like. Parenteral administration is usually by injection which may be subcutaneous, intramuscular or intravenous.

The compounds of this invention may be combined with other known anti-inflammatory/immunosuppressive agents such as steroids or non-steroidal anti-inflammatory agents (NSAID) in the pharmaceutical compositions and methods described herein.

The assay procedures by which useful biological activity of the compounds of the invention can be tested and/or demonstrated, are described below.

Calcium Channel (mobilization) Inhibition Assay

Polymorphonuclear leukocytes (PMNa), gastric glands, $GH_3$ cells, A431 cells, spleen cells, human keratinocytes corneal cells, etc. were loaded with the $Ca^{2+}$ sensitive fluorescent dye, Fura-2. The appropriate cell type was chosen and the potency and efficacy of the anti-inflammatory furanones on calcium mobilization, calcium channel inhibition was quantitated. The methods used for A431 cells listed below are representative of those used for other cells.

A431 cells were detached using a 5–10 min trypsin-EDTA treatment whereas $GH_3$ cells were treated 2 to 5 min with a 1% pancreatin solution. Cells were immediately washed twice in a 20 mM HEPES buffer (pH 7.4) containing 120 mM NaCl, 6 mM KCl, 1 mM $MgSO_4$, 1 mg/ml glucose and 1 mg/ml pyruvate and 1.4 mM calcium (medium A). Approximately $5 \times 10^6$ cells were suspended in medium A and incubated with 4 uM fura-2-AM for 15 min at 37° C.

After washing the fura-2 loaded cells, the uptake of dye was checked using fluorescence microscopy and found to be evenly distributed in the cytosol of all cells. Fluorescence was continuously recorded with a Perkin-Elmer LS-5 spectrofluorometer. The excitation wavelength was set at 340 nm and emission wavelength set at 500 nm. The cell suspension was continually stirred, maintained at 37° C. and equilibrated for approximately 5 min before addition of various agents. $[Ca^{2+}]i$ was calculated using the following formula:

$$[Ca^{2+}]_i = 220 \times \frac{F - F_{min}}{F_{max} - F}$$

All fluorescence values were measured relative to a EGTA-quenched signal determined as follows: F was the relative fluorescence measurement of the sample. $F_{max}$ was determined by lysing the cells with digitonin (100 ug/ml) in DMSO. After $F_{max}$ was determined the pH was adjusted to 8, with NaOH and $Ca^{2+}$ chelated with 3 mM EGTA to totally quench the fura-2 signal and obtain $F_{min}$.

When quin-2- was used, cells were incubated with 10 uM quin-2- at 37° C. for 1 hour, washed and then used.

Mouse Ear Anti-Inflammatory Assay

Test compound and phorbol myristate acetate (PMA) are topically applied simultaneously to the pinnae of the left ears of mice. PA alone is applied to the right ear. Three hours and 20 minutes after application, the mice are sacrificed, left and right ears removed, and standard sized bores taken. Edema (inflammation) is measured as the difference in weight between left and right ears [Van Arman, C. G., Clin Pharmacol Ther (1974) 16:900–904].

Inhibition of Phospholipase $A_2$

The effect of compounds of this invention on bee venom phospholipase $A_2$ is determined by the following procedure:

a. Bee venom phospholipase $A_2$ in 10 uM HEPES (pH 7.4) with 1 mM $CaCl_2$ is incubated with vehicle or test agent for 1.0 hour at 41°.

b. 1.36 mM phosphotidylcholine, 2.76 mM Triton X-100 are dispersed in buffer by sonication and then mixed with L-3 phosphotidylcholine, 1-palmitoyl-2-(1-$^{14}$C) palmitoyl for 10 min.

c. Start the reaction by the addition of enzyme (0.495 units/ml).

d. Incubation for 15 sec. at 41°.

e. Reaction is terminated by addition of 2.5 ml of isopropanol: n-heptane: 0.5M $H_2SO_4$ (40:10:1; v:v:v:).

f. 2.0 ml n-heptane and 1.0 ml $H_2O$ added; mixture centrifuged.

2.0 ml n-heptane removed and treated with 200–300 mg of silica gel HR60.

h. Samples centrifuged; 1 ml of n-heptane SN removed and added to 10 ml scintillation fluid.

i. Samples counted on a scintillation counter.

Activity Data

In the above-described phospholipase $A_2$ assay and Calcium$^{2+}$ channel mobilization assay the compounds of the invention were found to provide 50% inhibition ($IC_{50}$) at the following concentrations (in micromoles), as indicated in Table 1.

TABLE 1

| Phospholipase A2 Assay. | |
| --- | --- |
| Compound name or number (micromolar) | $IC_{50}$ |
| 1 | inactive at 3 μM |
| 2 | inactive at 3 μM |
| 3 | inactive at 3 μM |
| 4 | inactive at 3 μM |
| manoalide | 0.03 |
| Calcium$^{2+}$ Channel Mobilization Inhibition Assay | |
| | $IC_{50}$ (micromolar) |

TABLE 1-continued

| Compound name or number | TRH induced | KCl induced |
| --- | --- | --- |
| 1 | 6.4 | 0.36 |
| 2 | 1.0 | 0.25 |
| 3 | 0.67 | 0.47 |
| 4 | inactive | 8.0 |
| manoalide* | 0.6 | 0.8 |

*Data for manoalide are provided for comparison.

SPECIFIC EMBODIMENTS

The compounds of the present invention can be made by the synthetic chemical pathways which are illustrated here in general terms, by reference to U.S. Pat. No. 5,183,906 (the specification of which is expressly incorporated herein) and in the below given specific examples. The synthetic chemist will readily appreciate that the conditions described here in general terms, and specifically, can be generalized to any and all compounds represented by Formula 1. Furthermore, the synthetic chemist will readily appreciate that the herein described synthetic steps may be varied or adjusted by those skilled in the art without departing from the scope and spirit of the invention.

Generally speaking, the the compounds of the present invention which, in accordance with Formula 1 lack the 5-hydroxy function on the furan nucleus, can be obtained by reducing with sodium borohydride (or with a comparable mild reducing agent) the corresponding 5-hydroxy-2-furanone compounds. This general reaction is illustrated above in Reaction Scheme 1.

The 5-hydroxy 2-furanone compounds of Formula 2 which serve as starting materials for the reduction illustrated in Reaction Scheme 1 can be obtained in accordance with the synthetic procedures described in U.S. Pat. No. 5,183,906 ('906 patent).

Specifically, Reaction Scheme 2 and the accompanying pertinent description of the '906 patent disclose a synthetic process for preparing the 5-alkyl or phenyl substituted 5-hydroxy-2-furanone derivatives which can serve as the appropriately substituted starting materials of Formula 2 in Reaction Scheme 1 of the present disclosure.

Reaction Scheme 3 and the accompanying pertinent description of the '906 patent disclose a synthetic process for preparing the 3-alkyl substituted 5-hydroxy-2-furanone derivatives which can serve as the appropriate starting materials of Formula 2 in Reaction Scheme 1 of the present disclosure.

The starting materials of Formula 2 for the preparation of compounds of the present invention which are 3,5-dialkyl-2-furanone derivatives, can be made in accordance with the description provided in column 13 of the reference '906 patent.

The starting materials of Formula 2 for the preparation of compounds of the present invention which are 3-phenyl and 3-phenyl-5-alkyl-2-furanone derivatives, can be made in accordance with Reaction Schemes 4 and 5, respectively, and the attendant description and examples provided in the reference '906 patent.

As is described in the reference '906 patent, preparation of the 5-hydroxy-2-furanones starting materials of Formula 2 (of the this disclosure) normally includes a step of oxidation with singlet oxygen, which step utilizes Rose Bengal dye as a catalyst and requires irradiation by light. Generally speaking, the step of singlet oxidation is conducted on a precursor compound of Formula 2 which has a $Y_1$ substituent other than hydrogen, for example an alkyl or an acyl group. The $Y_1$ group is introduced with an alkylating, acylating, alkylsulfonylating reagent, with an isocyanate or with other appropriate reagent, to the hydroxyl function in the side chain of the 4-position of the furan nucleus. As it will become apparent from the ensuing specific examples, the $Y_1$ can also be introduced by an alkylating, acylating or other appropriate reagent to the hydroxyl function in the side chain of the 4-position on the furan nucleus after singlet oxidation, and after the reduction step pursuant to Reaction Scheme 1 has already been performed.

The reduction step of Reaction Scheme 1 can, generally speaking, be conducted on compounds of Formula 2 where $Y_1$ is either hydrogen or an alkyl or an acyl group. This reaction is typically conducted in an anhydrous ether-type solvent, such as tetrahydrofuran or ethylene glycol dimethyl ether, under a blanket of inert gas, such as argon, at room temparature or at 0° C., typically for 2 or 3 hours.

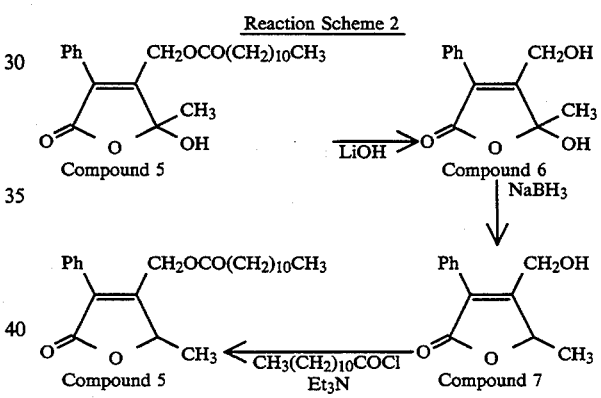

Reaction Scheme 2

The compound 4-dodecoyloxymethyl-5-hydroxy-5-methyl-3-phenyl-2-furanone (Compound 5) serves as the starting material for the preparation of Compound 4 of the present invention. The preferred synthetic procedure, illustrated in Reaction Scheme 2, for obtaining this compound involves the step of saponifying Compound 5, followed by reduction with sodium borohydride of the resulting 4-hydroxymethyl-5-hydroxy-5-methyl-3-phenyl-2-furanone (Compound 6) to yield Compound 7. Compound 7 is then subsequently reesterified by treatment with lauroyl chloride to yield Compound 4 of the invention.

The starting material 4-dodecoyloxymethyl-5-hydroxy-5-methyl-3-phenyl-2-furanone (Compound 5) is described in the reference '906 patent (see Column 27, lines 7–30) and can be prepared in accordance with the synthetic procedure disclosed in the reference '906 patent. The presently prefered procedure for obtaining relatively larger quantitities of Compound 5 differs, however, in certain steps and conditions from the procedure disclosed in the reference '906 patent, and is therefore described here in connection with Reaction Scheme 3.

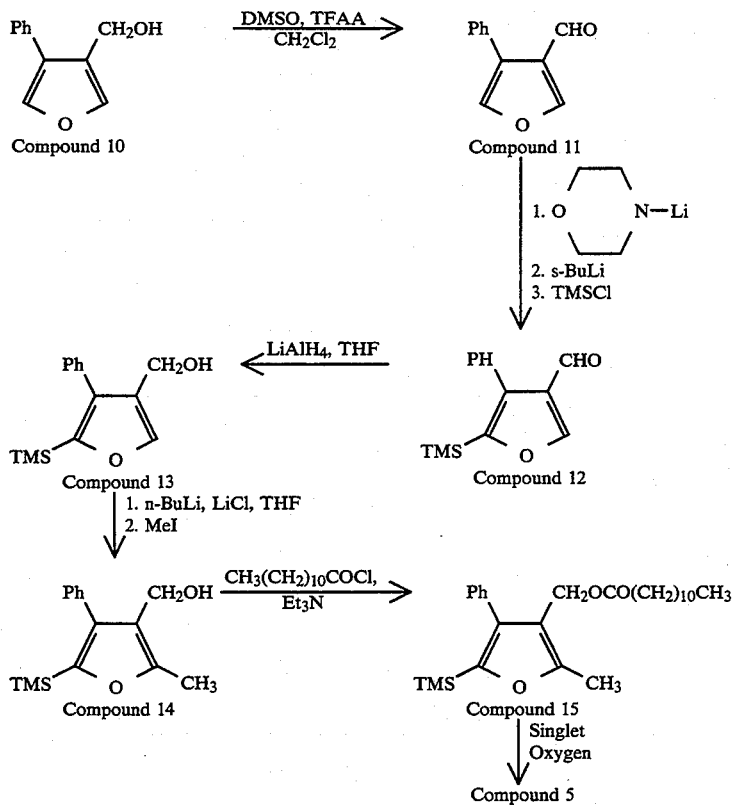

Reaction Scheme 3

In accordance with Reaction Scheme 3, 4-phenyl-3-furylcarbinol (Compound 10) is oxidized to yield 4-phenyl-3-furaldehyde (Compound 11), which is thereafter reacted sequentially with lithium morpholide, sec-butyl lithium and trimethylsilyl chloride to yield 4-phenyl-5-trimethylsilyl-3-furancarboxaldehyde (Compound 12). The first compound in this scheme, 4-phenyl-3-furylcarbinol (Compound 10) is described in the reference '906 patent (see column 24) and can be obtained from commercially available starting materials, in accordance with the procedure described in that patent, and also described here.

4-Phenyl-5-trimethylsilyl-3-furancarboxaldehyde (Compound 12) is reduced with lithium aluminum hydride to yield the corresponding alcohol (Compound 13), which is thereafter methylated with methyl iodide in the presence of n butyl lithium and lithium chloride in the 5-position of the furan nucleus to yield 5-trimethylsilyl-4-phenyl-3-hydroxymethyl-2-methylfuran (Compound 14). 5-Trimethylsilyl-4-phenyl-3-hydroxymethyl-2-methylfuran (Compound 14) is esterified by treatment with lauroyl chloride in the presence of triethylamine to yield 5-trimethylsilyl-4-phenyl-3-dodecoyloxymethyl-2-methylfuran (Compound 15). Compound 15 is subjected to singlet oxidation, in a chilled (approximately $-5°$ C.) dry tetrahydrofuran solution, in the presence of Rose Bengal dye under irradiation with light to provide 4-dodecoyloxymethyl-5-hydroxy-5-methyl-3-phenyl-2-furanone (Compound 5).

The following examples of specific compounds of the invention, and specific examples of the synthetic steps in which the compounds and certain intermediates are made, are set out to illustrate the invention, not to limit its scope.

SPECIFIC EXAMPLES 4-(1-Acetoxytridecyl)-3-methyl-2-furanone (Compound 2)

NaBH$_4$ (25 mg, 0.67 mmol) was added to a solution of 4-(1-acetoxytridecyl)-3-methyl-5-hydroxy-2(5-H)-furanone (157 mg, 0.44 mmol) in anhydrous THF (20 mL) at room temperature under argon. After 2 hours aqueous HCL (1N) was added carefully until pH2 was reached and the resulting mixture was stirred an additional 1 hour. This mixture was extracted with ethyl acetate and the combined organic fractions were washed with 5% sodium bicarbonate and brine. Evaporation of the dried (magnesium sulfate) extracts gave an oil which was purified by flash chromatography on silica using 30% ethyl acetate/hexane. Fractions with R$_f$ of about 0.45 on evaporation afforded the title compound.

IR (CHCl$_3$): 1753 cm$^{-1}$.

$^1$H NMR (CDCl$_3$): 0.88 (t, J=6.7 Hz, 3H), 1.19–1.38 (m, 20H), 1.58–1.72 (m, 1H), 1.73–1.88 (m, 1H), 1.91 (m, 3H), 2.09 (s, 3H), 4.66 (dd, J=17.2 Hz, J=2.0 Hz, 1H), 4.77 (dd, J=17.2 Hz, J=2.0 Hz, 1H), 5.69 (t, J=6.9 Hz, 1H).

$^{13}$C NMR (CDCl$_3$): 8.9, 14.0, 20.6, 22.5, 24.9, 29.0, 29.1, 29.2, 29.3, 29.4, 29.5, 31.8, 33.1, 68.9, 69.3, 124.6, 156.7, 169.8, 174.4.

Elemental analysis: theoretical carbon 70.97%, found 70.60%, theoretical hydrogen 10.12%, found 9.91%.

4-(1-Hydroxytridecyl)-5-hydroxy-5-methyl-2-furanone

LiOH (0.5M, 22.6 mL, 11.32 mmol) was added to a solution of 4-(1-acetoxytridecyl)-5-hydroxy-5-methyl-2-furanone (1.00 g, 2.83 mmol) in THF (15 mL). After stirring for 3 hours at room temperature the reaction was quenched with glacial acetic acid (680 mg, 11.3 mmol) and extracted with ethylacetate. The combined organic fractions were washed with a saturated solution of aqueous sodium bicarbonate, $H_2O$ and brine. Evaporation of the dried (magnesium sulfate) extracts gave an oil which was purified by flash chromatography on silica using 40% ethyl acetate/hexane to give the title alcohol.

IR ($CHCl_3$): 3376 (br), 1761 $cm^{-1}$ $^1$H NMR ($CDCl_3$), mixture of diastereomers: 0.88 (t, J=6.7 Hz, 3H), 1.2–1.6 (m, 20H), 1.65–1.90 (m, 5H), 2.4 (brs, 0.5H), 2.9 (brs, 0.5H), 4.3 (brs, 0.5H), 4.56 (brt, J=5.0 Hz, 1H), 4.8 (brs, 0.5H), 5.96 (S, 1H).

$^{13}$C NMR ($CDCl_3$), mixture of diastereomers: 14.1, 22.8, 24.2, 25.3, 29.3 29.5, 29.6, 31.9, 35.5, 66.7, 66.9, 68.0, 107.2, 107.3, 116.5, 171.2, 173.7.

Elemental analysis: theoretical carbon 69.19%, found 69.08%, theoretical hydrogen 10.33% found 10.60%.

4-(1-Hydroxytridecyl)-5-methyl-2(5H)-furanone (Compound 3)

$NaBH_4$ (210 mg, 5.54 mmol) was added in portions to a solution of 4-(1-hydroxytridecyl)-5-hydroxy-5-methyl-2-furanone (586 mg, 1.85 mmol) in anhydrous ethyle glycol dimethyl ether (60 mL) at 0° C. under argon. After stirring for 3 hours at 0° C. the reaction was quenched with HCl (6N) to pH2 and extracted with ethyl acetate. The combined organic fractions were washed with a saturated solution of aqueous sodium bicarbonate, $H_2O$ and brine. Evaporation of the dried (magnesium sulfate) extracts gave an oil which was purified by flash chromatography on silica using 30% ethyl acetate/hexane to give the title compound as a mixture of diastereomers. Recrystallization from diethyl ether/hexane gave a single diastereomer.

IR ($CHCl_3$): 1751 $cm^{-1}$.

$^1$H NMR ($CDCl_3$): 0.88 (t, J=6.7 Hz, 3H), 1.2–1.5 (m, 20H), 1.53 (d, J=6.7 Hz, 3H), 1.65 (brs, 1H), 1.66–1.86 (m, 2H), 4.51 (m, 1H), 5.20 (q, J=6.7 Hz, 1H), 5.86 (s, 1H).

$^1$H NMR ($CDCl_3$): 14.1, 18.7, 22.7, 25.1, 29.3, 29.4, 29.5, 29.6, 31.9, 35.6, 67.7, 79.8, 115.2, 172.8, 175.3.

Elemental analysis; theoretical carbon 71.83%, found 72.09%, theoretical hydrogen 10.89%, found 10.91%.

4-(1-Acetoxytridecyl)-5-methyl-2(5H)-furanone (Compound 1)

4-(1-Hydroxytridecyl)-5-methyl-2(5H)-furanone (Compound 3, 329 mg, 1.11 mmol), acetic anhydride (453 mg, 4.45 mmol), triethylamine (227 mg, 2.22 mmol) and 4-dimethylaminopyridine (2 mg, 0.02 mmol) were stirred at room temperature under argon for 3 hours in anhydrous THF (30 mL). The crude reaction mixture was concentrated and the residue was taken up in diethyl ether and washed with a 10% aqueous HCl solution, a saturated solution of sodium bicarbonate, $H_2O$ and brine. Evaporation of the dried (magnesium sulfate) extracts gave an oil which was purified by flash chromatography on silica using 20% ethyl acetate/hexane to give the title compound.

IR ($CHCl_3$): 1751 $cm^{-1}$.

$^1$H NMR ($CDCl_3$), mixture of diastereomers: 0.88 (t, J=6.6 Hz, 3H), 1.2–1.4 (m, 20H), 1.46 (d, J=6.8 Hz, 1.5H), 1.52 (d, J=6.8 Hz, 1.5H), 1.71 (m, 1H), 1.81 (m, 1H), 2.10 (s, 1.5H), 2.14 (s, 1.5H), 4.97 (dq, J=6.8 Hz, J=1.6 Hz, 0.5H), 5.11 (dq, J=6.8 Hz, J= 1.6 Hz, 0.5H), 5.52 (brt, J=6.6 Hz, 0.5H), 5.57 (m, 0.5H), 5.89 (m, 0.5H), 5.47 (m, 0.5H).

$^{13}$C NMR ($CDCl_3$), mixture of diastereomers: 13.9, 18.3, 18.5, 20.6, 22.5, 24.6, 24.9, 29.0, 29.1, 29.2, 29.3, 29.4, 31.7, 32.9, 33.4, 68.4, 69.4, 78.3, 79.0, 115.3, 117.3, 169.6, 169.9, 170.6, 171.5, 171.6, 171.7.

Elemental analysis: theoretical carbon 70.97%, found 71.09%. Theoretical hydrogen 10.12%, found 10.32%.

4-Hydroxymethyl-5-hydroxy-5-methyl-3-phenyl-2-furanone (Compound 6)

LiOH (0.5M, 19.7 mL, 9.83 mmol) was added to a solution of 4-dodecoyloxymethyl-5-hydroxy-5-methyl-3-phenyl-2-furanone (Compound 5, see improved process for preparation below), in THF (20 mL) at room temperature. After stirring for 3 hours the reaction was quenched with glacial acetic acid (590 mg, 9.83 mmol) and the THF was removed by rotary evaporator. Solids were removed from the residual aqueous slurry. The clear aqueous solution containing the crude product was lyophylized, adhered to silica with methanol and purified by flash chromatography using 60% ethyl acetate/hexane to give the title alcohol.

IR ($CHCl_3$): 3300, 3023, 1766 $cm^{-1}$.

$^1$H NMR ($CDCl_3$): 1.76 (s, 3H), 3.3 (vbrs, 1H), 4.57 (s, 2H), 5.7 (vbrs, 1H), 7.32 to 7.42 (m, 5H).

$^{13}$C NMR ($CDCl_3$): 24.2, 56.2, 105.5, 128.3, 128.5, 129.1, 129.3, 158.3, 170.5.

LRMS: m/x observed at 220 (M+).

4-Hydroxymethyl-5-methyl-3-phenyl-2(5H)-furanone (Compound 7)

To $NaBH_4$ (147 mg, 3.88 mmol) suspended in anhydrous ethylene glycol dimethyl ether (20 mL) at 0° C. under argon was added 4-hydroxymethyl-5-hydroxy-5-methyl-3-phenyl-2-furanone (Compound 6) in ethylene glycol dimethyl ether (20 mL) dropwise. After stirring for 3 hours the solution was acidified to pH2 with 6N HCl, warmed to ambient temperature and stirred an additional 1 hour. The solution was concentrated to 10 mL volume and the organics were extracted into ethyl acetate. The combined organic fractions were washed with a saturated solution of aqueous sodium bicarbonate, $H_2O$ and brine. Evaporation of the dried (magnesium sulfate) extracts gave an oil which was purified by flash chromatography on silica using 30% ethyl acetate/hexane to give the title compound.

IR ($CHCl_3$): 3616, 3300 (v. br.), 3022, 1747 $cm^{-1}$.

$^1$H NMR ($CDCl_3$): 1.54 (d, J=6.8 Hz, 3H), 3.38 (m, 1H), 4.54 (dd, J=6.1 Hz, J=14.9 Hz, 1H), 4.70 (dd, J=3.9 Hz, J=14.9 Hz, 1H), 5.24 (q, J=6.8 Hz, 1H), 7.3–7.43 (m, 5H).

$^{13}$C NMR ($CDCl_3$): 18.3, 57.0, 78.2, 126.0, 128.4, 128.8 129.1, 164.6, 172.9.

LRMS: m/z observed at 204 (M+).

4-Dodecoyloxymethyl-5-methyl-3-phenyl-2(5H)-furanone (Compound 4)

4-Hydroxymethyl-5-methyl-3-phenyl-2(5H)-furanone (Compound 7), (73 mg, 0.36 mmol), lauroyl chloride (117 mg, 0.54 mmol), triethylamine (47 mg, 0.47 mmol) and dimethylaminopyridine (1 mg, 0.01 mmol) were stirred in anhydrous THF (2 mL) at ambient temperature under argon for 2 hours. The crude reaction mixture was concentrated, the organics were extracted into diethyl ether and solids were filtered off. The ether was removed by rotary evaporator and the resulting oil was purified by flash chromatography on silica to give the title compound.

IR ($CHCl_3$): 3027, 1751 $cm^{-1}$.

$^1$H NMR ($CDCl_3$): 0.88 (t, J=6.6 Hz, 3H), 1.15 to 1.37 (m, 16H), 1.56 (d, J=6.7 Hz, 3H), 1.61 (m, 2H), 2.32 (m, 2H), 5.07 (d, J=4.4 Hz, 2H), 5.15 (q, J=6.7 Hz, 1H), 7.36–7.49 (m, 5H).

$^{13}$C NMR (CDCl$_3$): 14.0, 18.4, 22.6, 24.7, 29.0, 29.1, 29.2, 29.3, 29.5, 31.8, 33.8, 57.9, 77.4, 128.5, 128.8, 128.9, 129.1, 129.2, 157.6, 171.3, 172.9.

Elemental analysis: theoretical carbon 74.58% found 74.58%; theoretical hydrogen 8.87%, found 8.59%.

Improved Preparation of 4-dodecoyloxymethyl-5-hydroxy-5-methyl-3-phenyl-2-furanone (Compound 5)

| Step 1. Preparation of 4-Phenyloxazole. | | | |
|---|---|---|---|
| | Amount | MW | moles |
| 2-Bromoacetophenone | 40 g | 199.05 | 0.2 |
| Ammonium Formate | 44 g | 63.06 | 0.7 |
| Formic Acid | 210 mL | | |

A mixture of 2-bromoacetophenone and ammonium formate in formic acid was stirred at reflux under nitrogen for 2 hours. The cooled reaction mixture was treated with 400 mL of H$_2$O and extracted with ether (3×200 mL). The combined organics were washed with saturated aqueous NaHCO$_3$, dried over MgSO$_4$, filtered and concentrated under reduced pressure. The residue was purified by column chromatography (eluting with EtOAc/hexanes, 1:9) to afford 8.9 g (31%) of 4-phenyloxazole as a yellow oil.

| Step 2. Ethyl-4-phenylfuran-3-carboxylate. | | | |
|---|---|---|---|
| | Amount | MW | moles |
| 4-Phenyloxazole | 8.86 g | 145 | 0.061 |
| Ethyl phenylpropiolate | 10.6 g | 174.2 | 0.061 |

A mixture of 4-phenyloxazole and ethyl phenylpropiolate was heated at 200°–210° C. in a sealed tube under N$_2$ for 22 hours. The cooled reaction mixture was purified by column chromatography (eluent, CH$_2$Cl$_2$/hexanes, 1:1) to give 12.65 g (96%) of adduct as a red oil which was contaminated with phenylacetonitrile. Although the product obtained in this preparation was not 100% pure, it was used in the next step without further purification.

| Step 3. (4-Phenyl-3-furyl)carbinol (Compound 10) | | | |
|---|---|---|---|
| | Amount | MW | moles |
| ethyl-4-phenylfuran-3-carboxylate | 12.65 g | 216 | 0.059 |
| LiAlH$_4$ | 1.23 g | 37.95 | 0.033 |
| THF | 180 + 30 mL | | |

To the solution of ethyl-4-phenylfuran-3-carboxylate in dry THF (180 mL, freshly distilled from Na/benzophenone) was added dropwise the suspension of lithium alumium hydride in THF (30 mL) at 0° C. under nitrogen. Then the mixture was warmed to room temperature and quenched with 1N HCl acid and extracted with EtOAc. The organic layer was washed with brine, dried over MgSO$_4$, filtered and concentrated under reduced pressure. The residue was purified by column chromatography (eluent, CH$_2$Cl$_2$) to afford 6.1 g (59%) of (4-phenyl-3-furyl)carbinol as white crystals.

| Step 4. 4-Phenyl-3-furancarboxaldehyde (Compound 11) | | | |
|---|---|---|---|
| | Amount | MW | moles |
| Compound 10 | 9.39 g | 174 | 0.054 |
| DMSO | 8.44 g (7.7 ml) | 78.13 | 0.108 |
| TFAA | 20.94 g | 210.03 | 0.081 |
| iPr$_2$NEt | (28 ml) 20.94 g (28 ml) | 129.25 | 0.162 |
| CH$_2$Cl$_2$ | 60 + 10 + 40 mL | | |

To a solution of DMSO (distilled from CaH$_2$) in dry CH$_2$Cl$_2$ (60 mL, distilled from CaH$_2$) was added dropwise trifluoroacetic anhydride in dry CH$_2$Cl$_2$ (10 mL) under nitrogen at −78° C. over approximately 15 minutes. The mixture was stirred at −78° C. for an additional 15 minutes. To the slurry was then added dropwise the starting material in dry CH$_2$Cl$_2$ (40 mL) at −78° C. over approximately 20 minutes. The yellow solution was stirred at −78° C. for 1 hour. The iPr$_2$NEt was then added at −78° C. and the solution was warmed gradually to room temperature. The reaction mixture was washed sequentially with 1N HCl and saturated aqueous NaHCO$_3$, dried over MgSO$_4$, filtered and concentrated under reduced pressure. The residue was purified by column chromatography (EtOAc/hexanes, 1:4) to give 8.88 g (96%) of 4-phenyl-3-furancarboxaldehyde (Compound 11) as a yellow oil.

| Step 5. 4-Phenyl-5-trimethylsilyl-3-furancarboxaldehyde (Compound 12) | | | |
|---|---|---|---|
| | Amount | MW | moles |
| Compound 11 | 8.35 g | 172 | 0.049 |
| morpholine | 4.44 g | 87.12 | 0.051 |
| n-BuLi, 2.5 M in hexanes | 20.4 mL | | 0.051 |
| s-BuLi, 1.3 M in cyclohexane | 44.8 mL | | 0.058 |
| TMSCl | 7.91 g | 108.64 | |
| THF | 60 + 40 mL | | |

To the solution of morpholine (freshly distilled from CaH$_2$) in dry THF (60 mL) was added dropwise n-BuLi at 0° C. under nitrogen. The resulting solution was stirred at 0° C. for an additional 15 minutes then cooled to −78° C., and aldehyde (Compound 11) in dry THF (40 mL) was added dropwise. The mixture was warmed to 0° C. and stirred at 0° C. for 15 minutes, then the mixture was recooled to −78° C., and the s-BuLi was added dropwise. The resulting slurry was stirred at −78° C. and the reaction mixture was gradually warmed to room temperature. The reaction mixture was quenched with saturated aqueous NH$_4$Cl and extracted with EtOAc. The organic layer was dried over MgSO$_4$, filtered and concentrated under reduced pressure. The residue was purified by column chromatography (eluent, EtOAc/hexanes, 1:4) to give 8.08 g (68%) of 4-phenyl-5-trimethylsilyl-3-furancarboxaldehyde (Compound 12) as a yellow oil.

| Step 6. (4-Phenyl-5-trimethylsilyl-3-furyl)carbinol (Compound 13) | | | |
|---|---|---|---|
| | Amount | MW | moles |
| Compound 12 | 8.08 g | 244 | 33 |
| LiAlH$_4$ (1.0 M in THF) | 14.4 mL | | 12.4 |
| THF | 80 mL | | |

To the solution of trimethylsilyl-aldehyde (Compound 12) in dry THF was added dropwise the LiAlH$_4$ solution at 0° C. under nitrogen. The reaction mixture was stirred at 0° C. for 1 hour, then quenched with 1N HCl (60 mL) and extracted with EtOAc. The organic layer was washed with brine, dried over MgSO₄, filtered and concentrated under reduced pressure. The residue was purified by column chromatography (EtOAc/hexane, 1:4) to give 6.75 g (83%) of the title compound as a yellow oil.

| Step 7. 5-Trimethylsilyl-4-phenyl-3-hydroxymethyl-2-methylfuran (Compound 14) | | | |
|---|---|---|---|
|  | Amount | MW | moles |
| Compound 13 | 6.8 g | 246 | 0.028 |
| n-BuLi, 2.5 M in hexanes | 25 mL |  | 0.063 |
| LiCl | 11.72 g | 42.4 | 0.28 |
| MeI | 19.6 g | 141.9 | 0.14 |
| THF | 120 mL |  |  |

To the solution of Compound 13 in dry THF was added dropwise n-BuLi at −78° C. under nitrogen. The reaction mixture was gradually warmed to −20° C., and the LiCl was added at −20° C., followed by MeI (freshly distilled). The mixture was stirred at −20° C. for 24 hours, then quenched with saturated aqueous NH₄Cl, and extracted with EtOAc. The organic layer was dried over MgSO₄, filtered and concentrated under reduced pressure. The residue was purified by column chromatography (eluent, EtOAc/hexanes, 1:4) to give 6.37 g of product as a yellow oil. The product was contaminated with the 2-desmethyl compound (starting material) but was suitable for the next reaction step. (Ratio of product to starting material, approximately 4:1 by proton NMR integration, corresponding to 71% yield of product).

| Step 8. 5-trimethylsilyl-4-phenyl-3-dodecoyloxymethyl-2-methylfuran (Compound 15) | | | |
|---|---|---|---|
|  | Amount | MW | moles |
| Compound 14 | 6.1 g | 260 | 0.0235 |
| lauroyl chloride | 10.26 g | 218.77 | 0.047 |
| Triethylamine | 4.75 g | 101.19 | 0.047 |
| THF | 100 mL |  |  |

To the solution of Compound 14 in dry THF was added triethylamine at 0° C. under nitrogen, followed by lauroyl chloride. The mixture was stirred at 0° C. for 1 hour, then treated with water and extracted with ether. The organic layer was washed with brine, dried over MgSO₄, filtered and concentrated under reduced pressure. The residue was purified by column chromatography (eluent, EtOAc/hexanes, 1:25) to give 12.14 g of product as a colorless oil in quantitative yield. This product was contaminated with its corresponding desmethyl analog.

| Step 9. 4-dodecoyloxymethyl-5-hydroxy-5-methyl-3-phenyl-2-furanone (Compound 5) | | | |
|---|---|---|---|
|  | Amount | MW | moles |
| Compound 15 | 13.66 g | 442.27 | 31 |
| Rose Bengal | 50 mg |  | 0.05 |
| THF | 1200 mL |  |  |

The solution of Compound 15 and Rose Bengal in THF was saturated with O₂, then cooled to approximately −5° C. (dry ice/acetone bath) and irradiated with a 150 watt flood lamp (maintaining the temperature of the mixture at −5° to 0° C.) for 3 hours. The reaction mixture was then filtered and concentrated to a pink oil which was purified by column chromatography (eluent, EtOAc/hexanes, 1:20 to 1:4) to give 3.4 g (27%) of pure title compound as a colorless oil. An additional 3 g (approximately 25%) of a mixture of the title compound and the 5-desmethyl derivative (ratio 1:1 by proton NMR integration) was also obtained as a yellow oil.

What is claimed is:

1. A compound of the formula

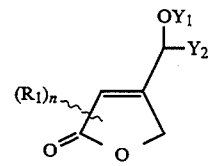

where $R_1$ is alkyl of 1 to 9 carbons;

n is an integer having the values of 1 or 2, when n is 1 the $R_1$ group is attached to the 5 position of the 2-furanone, when n is 2 then $R_1$ is attached to both the 3 and 5 positions;

$Y_1$ is H, alkyl of 1 to 20 carbons, phenyl $C_1$–$C_{20}$ alkyl, $C_1$–$C_{20}$ alkenyl containing one or more olefinic bonds, $PO(OH)_2$, $PO(OH)OR_2$, $PO(OH)R_2$, $PO(OR_2)_2$, where $R_2$ is independently alkyl of 1 to 20 carbons, phenyl, halogen substituted phenyl or $C_1$–$C_6$ alkyl substituted phenyl, further $Y_1$ is CO—$R_3$, CO—$OR_3$, $CONHR_3$, $SO_2R_3$, $SO_2NHR_3$, $(CH_2)_p$—O—$R_3$, or $(CH_2)_p$—O—$(CH_2)_m$—O—$R_3$, where p, and m, are integers and are independently 1 to 20 and $R_3$ is H, $C_1$–$C_{20}$ alkyl, $C_1$–$C_{20}$ alkenyl containing one or more olefinic bonds, phenyl, halogen substituted phenyl or $C_1$–$C_6$ alkyl substituted phenyl, with the proviso that when $Y_1$ is CO—$OR_3$ or $CONHR_3$ then $R_3$ is not hydrogen, and $Y_2$ is H, an alkyl group of 1 to 25 carbons, phenyl, naphthyl, phenyl ($C_1$–$C_{20}$)alkyl-, naphthyl ($C_1$–$C_{20}$)alkyl-, halogen substituted phenyl, $C_1$–$C_6$ alkyl substituted phenyl, halogen substituted naphthyl, $C_1$–$C_6$ substituted naphthyl.

2. A compound of claim 1 where $R_1$ is lower alkyl.
3. A compound of claim 1 where n is 1.
4. A compound of claim 1 where n is 2.
5. A compound of claim 1 where $Y_1$ is H.
6. A compound of the formula

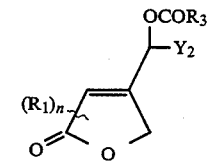

where $R_1$ independently is H, phenyl, $C_1$–$C_6$ alkyl substituted phenyl, halogen substituted phenyl, or alkyl of 1 to 9 carbons;

n is an integer having the values of 1 or 2, when n is 1 the $R_1$ group is attached either to the 3 or to the 5 position of the 2-furanone, when n is 2 then $R_1$ is attached to both the 3 and 5 positions, with the proviso that the substituents in the 3 and 5 positions both cannot be hydrogen;

$Y_2$ is H, an alkyl group of 1 to 25 carbons, phenyl, naphthyl, phenyl, ($C_1$–$C_{20}$)alkyl-, napthyl, ($C_1$–$C_{20}$)alkyl-, halogen substituted phenyl, $C_1$–$C_6$ alkyl substituted phenyl, halogen substituted naphthyl, $C_1$–$C_6$ substituted naphthyl.

7. A compound of claim 1 where $Y_2$ is H.

8. A compound of claim 1 where $Y_2$ is alkyl having 4 to 25 carbons.

9. A compound of claim 6 where $Y_2$ is H and $R_3$ is alkyl having 4 to 25 carbons.

10. A compound of claim 6 where $Y_2$ is alkyl having 4 to 25 carbons and $R_3$ is $CH_3$.

11. A compound of the formula

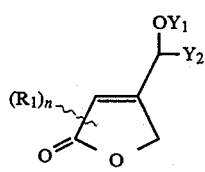

where $R_1$ is lower alkyl,
n is an integer having the values of 1 or 2, when n is 1 the $R_1$ group is attached to the 5 position of the 2-furanone, when n is 2 then $R_1$ is attached to both the 3 and 5 positions;
$Y_1$ is H or $CH_3CO$, and
$Y_2$ is an alkyl group of 8 to 16 carbons.

12. A compound of claim 11 where n is 1, and $R_1$ is 5-methyl.

13. A compound of claim 12 where $Y_2$ is $CH_3(CH_2)_{11}$.

14. The compound of the formula

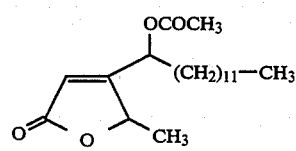

15. The compound of claim 12 where $Y_1$ is H.

16. A compound of claim 11 where n is 1, and $R_1$ is 3-methyl.

17. The compound of the formula

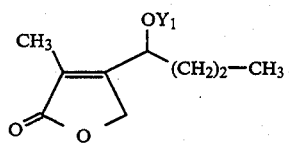

where $Y_1$ is H or $CH_3CO$.

18. The compound of claim 17 where $Y_1$ is $CH_3CO$.

19. A compound of the formula

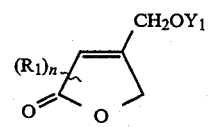

where $R_1$ independently is H, lower alkyl or phenyl,
n is an integer having the values of 1 or 2, when n is 1 the $R_1$ group is attached either to the 3 or to the 5 position of the 2-furanone, when n is 2 then $R_1$ is attached to both the 3 and 5 positions, with the proviso that the substituents in the 3 and 5 positions both cannot be hydrogen;
$Y_1$ is $R_3CO$ where $R_3$ is alkyl of 4 to 25 carbons.

20. A compound of claim 19 where n is 2, one of the $R_1$ groups is methyl and the other is phenyl.

21. A compound of claim 20 where the phenyl group is in the 3 position and the methyl group is in the 5 position.

22. The compound of claim 21 where the $R_3$ group is $CH_3(CH_2)_{11}$.

* * * * *

UNITED STATES PATENT AND TRADEMARK OFFICE
CERTIFICATE OF CORRECTION

PATENT NO. : 5,451,686
DATED : September 19, 1995
INVENTOR(S) : Garst

It is certified that error appears in the above-indentified patent and that said Letters Patent is hereby corrected as shown below:

Column 5, line 15, "Stil more more" should be --still more--;

Column 8, line 1, "[$Ca^{2+}$i" should be --[$Ca^{2+}$]$_i$--;

Column 9, line 26, "the the compounds" should be --the compounds--;

Column 9, line 67, "of the this disclosure" should be --of this disclosure--;

Column 12, line 43, "HCL" should be --HCl--;

Column 14, line 48, "128.8 129.1" should be --128.8, 129.1--.

Column 5, line 62, "$GH_3$cells" should be --$GH_3$ cells--;
Column 14, line 46, "7.3-7.43" should be --7.30-7.43.

Signed and Sealed this

Third Day of December, 1996

Attest:

BRUCE LEHMAN

Attesting Officer  Commissioner of Patents and Trademarks